United States Patent [19]

Arcamone et al.

[11] 4,021,601
[45] May 3, 1977

[54] PAROMOMYCIN DERIVATIVES AND PROCESS FOR THE PREPARATION THEREOF

[75] Inventors: Federico Arcamone, Milan; Giuseppe Cassinelli, Voghera, both of Italy

[73] Assignee: Societa' Farmaceutici Italia S.p.A., Milan, Italy

[22] Filed: Apr. 7, 1975

[21] Appl. No.: 565,657

[30] Foreign Application Priority Data

Apr. 11, 1974 Italy ................................. 21250/74

[52] U.S. Cl. ................................. 536/17; 424/180
[51] Int. Cl.² ........................................ C07H 15/22
[58] Field of Search ............. 260/210 AB, 210 NE; 536/17

[56] References Cited

UNITED STATES PATENTS 3,350,387  10/1967  Vanderhaeghe ............ 260/210 AB

OTHER PUBLICATIONS

Magyar et al., "Chem. Abst." vol. 74, 1971, p. 51831g.

*Primary Examiner*—Johnnie R. Brown
*Attorney, Agent, or Firm*—Stevens, Davis, Miller & Mosher

[57] ABSTRACT

A process is disclosed for preparing paromomycin derivatives N-substituted in the 2'-position and having the general formula:

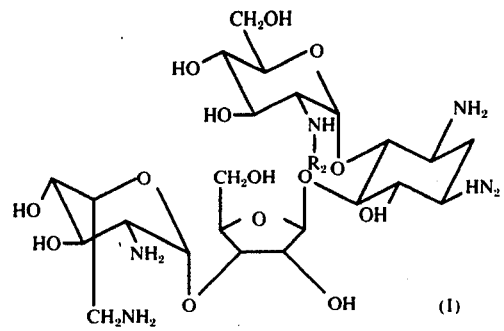

wherein $R_2$ is an alkyl radical having from 1 to 10 carbon atoms or an arylalkyl radical having not more than 10 carbon atoms, wherein paromomycin is treated with a carboxylic acid anhydride in the presence of a strong acid to give an intermediate of formula II as shown in the accompanying specification, which then is reacted in the presence of sodium borohydride with the aldehyde whose radical is to be attached to the N-atom in the 2' position. Also as new compounds, 2'-N-alkyl-paromomycins of formula (I), wherein $R_2$ is an alkyl radical having from 1 to 10 carbon atoms or an arylalkyl radical having not more than 10 carbon atoms, including
  tetra-(N-1, N-3, N-2''', N-6''')-acetylparomomycin;
  2'-N-ethylparomomycin; and
  2'-N-(3-phenylpropyl)-paromomycin.

The new compounds are useful as antibiotics.

5 Claims, No Drawings

PAROMOMYCIN DERIVATIVES AND PROCESS FOR THE PREPARATION THEREOF

The present invention relates to new paromomycin derivatives and to a process for the preparation thereof.

More precisely, the present invention relates to new paromomycin derivatives N-substituted in the 2'-position having the following formula:

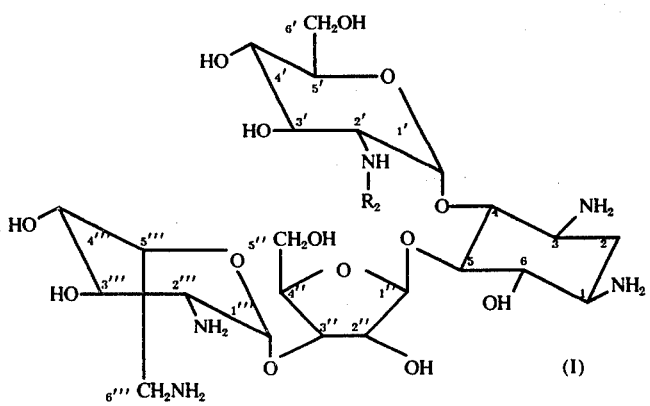

wherein $R_2$ is a lower alkyl radical having from 1 to 10 carbon atoms or an arylalkyl radical having not more than 10 carbon atoms.

Paromomycin is an antibiotic relating to the aminosaccharide field whose properties have been described in Frohardt et al U.S. Pat. No. 2,916,485. Arcamone et al U.S. Pat. No. 3,065,147 describes and claims a new fermentative process for obtaining paromomycin.

It is furthermore known that the toxicity and side-effects of this antibiotic are due to the number of primary amino groups present in the molecule. Penasse et al (Bull. Soc. Chim. France 1969, p. 2391) carried out a selective N-alkylation in the 6'''-position of paromomycin by sodium borohydride reduction of the corresponding Schiff's base. This method, however, does not afford selective substitution on primary amino groups which are not linked to a primary carbon atom.

German Patent Application No. 2,322,576 describes a method for acylating paromomycin in 1-position by protecting the amino group in position 6'''. This was one of the first attempts to substitute difficultly reactive amino groups of the antibiotic in question.

It has been now found (and this is object of the present invention) that it is possible in such a compound to obtain derivatives of a primary amino group attached to a secondary carbon atom, that is derivatives N-substituted in 2'-position. These paromomycin derivatives represent a further object of the invention in view of our discovery that they display antibiotic activity and can be employed as intermediates for further substitutions on free amino and hydroxy groups of paromomycin.

In order to obtain such paromomycin derivatives it is necessary to have a suitable intermediate, and this is prepared by the N-acylation of paromomycin with the anhydride of a lower aliphatic acid, as for example acetic anhydride, in the presence of an equivalent molecular weight of a strong acid, such as hydrochloric acid. More particularly, paromomycin is dissolved in a suitable solvent (for example, methanol) and then treated with a strong acid and acetic anhydride. The mixture is allowed to stand at room temperature and the precipitate thus formed is isolated and purified. The intermediate thus obtained corresponds to the formula:

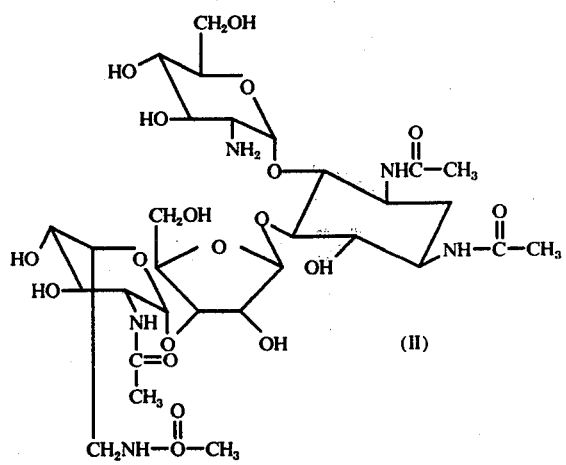

which is then converted into the desired compounds. For this purpose, compound (II) is reacted with the aldehyde whose radical is to be attached to the N-atom in 2'-position and the corresponding Schiff's base is reduced with sodium borohydride to the desired compound. The following examples illustrate the invention without limiting it.

EXAMPLE 1

Tetra-(N-1, N-3, N-2''', N-6''')-acetylparomomycin (II)

To 20 g of paromomycin (free base) dissolved in 800 ml of methanol, 32.5 of 1N aqueous hydrochloric acid were added. At 0° C, and while stirring, 100 ml of acetic anhydride were added. The mixture was kept overnight at room temperature, whereupon the crude product was precipitated with acetone. The crude product was purified by dissolving it in a mixture of 2% aqueous ammonium hydroxide and methanol which was then charged on a salicylic acid column (7.5 × 80 cm) using the above solvent mixture as eluent. The solvent was evaporated, and 14.5 g of (II), melting at 200° C (decomposition) were obtained after precipitation with acetone. $[\alpha]_D^{23°} = +60.5°$ (c = 1, MeOH).

EXAMPLE 2

2'-N-ethylparomomycin (I, $R_2 = C_2H_5$)

A solution of 2.7 g of (II) in 8 ml of distilled water was adjusted to pH 8.5 with a 10% solution of $NaHCO_3$ and then treated while shaking at 4° C with a solution of acetaldehyde in 8 ml of distilled water. After 20 minutes the reaction mixture was treated with a solution of 0.62 g of sodium borohydride in 11 ml of water. The whole was stirred for an hour, and then the reaction mixture was treated with a solution of sodium hydroxide in water. The mixture was refluxed for 6 hours at 135° C, cooled, the pH adjusted at 10.5 with dilute sulphuric acid, and the solution extracted with n-butyl alcohol in presence of benzaldehyde. The butanol extract was washed with water and extracted again with dilute sulphuric acid. The aqueous extract was washed with ether and adjusted to pH 5.5 with a solution of triethylamine; it was then concentrated and precipitated with methanol in excess.

2 g of the crude product were thus obtained. This was dissolved in water and chromatographed on an activated carbon-diatomaceous earth (1:1) column, which was previously treated with aqueous sulphuric acid and washed with water to pH 3.5. Water was used as eluent. After neutralization with triethylamine, evaporation of the solvent, and precipitation with methanol, 1.40 g of the 2'-N-ethylparomomycin product (as sulphate) were obtained: m.p. 285° C (decomposition) $[\alpha]_D^{23°} = +36$ (c = 0.55, $H_2O$).

EXAMPLE 3

2'-N-3-phenylpropylparomomycin (I, $R_2 = (CH_2)_3$—Ph)

A solution of 1 g of (II) in 4 ml of distilled water was adjusted to pH 8.5 with a 10% aqueous solution of sodium bicarbonate, and then treated while shaking with 0.6 ml of 3-phenylpropionaldehyde. The mixture was stirred for an hour at 0° C, treated with 400 mg of sodium borohydride in 8 ml of water, and shaken again for an hour. The reaction mixture was then treated with a solution of 2.5 g of sodium hydroxide in 35 ml of water and refluxed at 135° C.

Operating as described in Example 2, 0.65 g of the crude product (as sulphate) were obtained. This was charged on a column as described in Example 2, except that now the eluent was a mixture of aqueous 0.01N hydrochloric acid and methanol (1:1). After neutralization with triethylamine, the eluate was concentrated, treated with triethylamine sulphate in methanol, and precipitated with methanol in excess. 0.35 g of the product (as sulphate) was obtained, m.p. 270° C (decomposition) $[\alpha]_D^{23°} = +46.5°$ (c = 0.3, $H_2O$).

The minimal inhibitory doses (MID) of 20'-N-3-phenylpropylparomomycin and of 20'-N-ethylparomomycin are given in the following table against a variety of Gram-positive and Gram-negative bacteria in order to show the antibacterial activity of the new derivatives of the present invention. The conventional two-fold agar dilution method was used, with paromomycin as the comparison substance.

TABLE

In vitro antimicrobial activities of paromomycin derivatives, MID γ/ml

| Compound | Staphylococcus aureus 209 P | Escherichia coli B | Salmonella abortivo equino |
|---|---|---|---|
| 2'-N-3-phenylpropyl-paromomycin | 3.1 | 25 | 50 |
| 2'-N-ethylparomomycin | 3.1 | 25 | 25 |
| Paromomycin | 6.2 | 25 | 25 |

What is claimed is:

1. A 2'-N-alkylparomomycin or 2'N-phenylpropyl-paromomycin of formula (I):

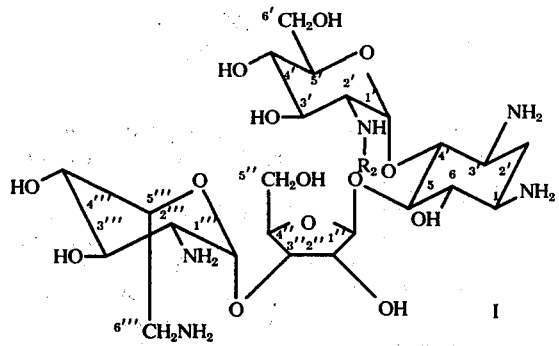

wherein $R_2$ is an alkyl radical having from 1 to 4 carbon atoms or a phenylpropyl radical.

2. Tetra-(N-1, N-3, N-2''', N-6''')-acetylparomomycin.

3. 2'-N-ethylparomomycin.

4. 2'-N-(3-phenylpropyl)-paromomycin.

5. A process for preparing a paromomycin derivative that is N-substituted selectively only in the 2'-position and has the general formula:

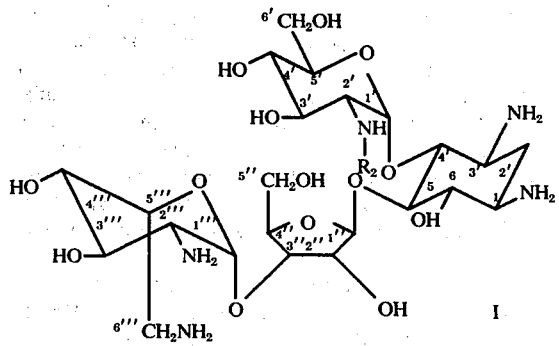

wherein $R_2$ is an alkyl radical having from 1 to 4 carbon atoms or a phenylpropyl radical, which comprises treating paromomycin with acetic anhydride in the presence of hydrochloric acid or sulphuric acid to give a compound of formula (II) having acetyl protecting groups in the N-1, N-3, N-2''' and N-6''' positions:

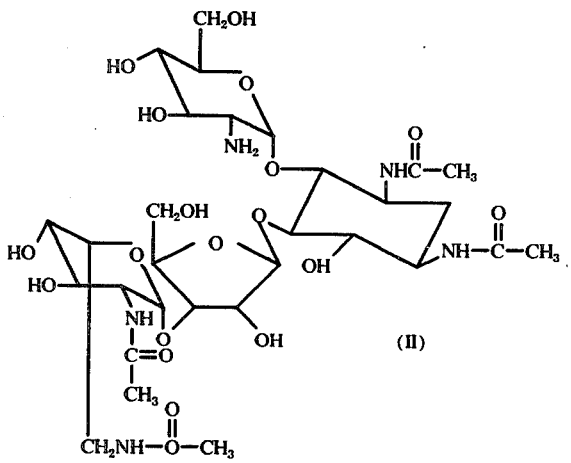

reacting the compound of formula (II) so obtained with phenylpropionaldehyde or an aliphatic aldehyde having from 1 to 4 carbon atoms in the presence of sodium borohydride in order to alkylate selectively only the N-atom in the 2' position, and then eliminating the acetyl protecting groups in the N-1, N-3, N-2''' and N-6''' positions wtih sodium hydroxide to give the desired compound of formula (I).

* * * * *

UNITED STATES PATENT OFFICE
CERTIFICATE OF CORRECTION

Patent No. 4,021,601    Dated May 3, 1977

Inventor(s) Federico ARCAMONE et al

It is certified that error appears in the above-identified patent and that said Letters Patent are hereby corrected as shown below:

In the Abstract, in structural formula I, on the far right side, delete "$HN_2$" and insert in its place --$NH_2$--;

Column 2, in structural formula II, bottom line, delete "$CH_2NH-O-CH_3$" and insert in its place --$CH_2NH-C-CH_3$--;

Column 2, line 65, delete "salicyclic" and insert in its place --silicic--;

Column 3, line 60, delete "20'-N-3-" and insert in its place -- 2'-N-3- --;

Column 3, line 61, delete "20'-N-ethylparomo-" and insert in its place -- 2'-N-ethylparomo- --;

Column 5, in structural formula II, last line, delete "$CH_2NH-O-CH_3$" and insert in its place --$CH_2NH-C-CH_3$--.

Signed and Sealed this

Eleventh Day of October 1977

[SEAL]

Attest:

RUTH C. MASON
Attesting Officer

LUTRELLE F. PARKER
Acting Commissioner of Patents and Trademarks